United States Patent [19]

Talonn

[11] Patent Number: 4,693,256
[45] Date of Patent: Sep. 15, 1987

[54] RESPIRATORY DEVICE

[75] Inventor: Daniel A. Talonn, University City, Mo.

[73] Assignee: Sherwood Medical Company, St. Louis, Mo.

[21] Appl. No.: 392,845

[22] Filed: Jun. 28, 1982

[51] Int. Cl.⁴ .................................. A61B 5/08
[52] U.S. Cl. ............................. 128/725; 128/727
[58] Field of Search .......... 128/725, 727; 272/99; 73/202, 239

[56] References Cited

U.S. PATENT DOCUMENTS

| | | | |
|---|---|---|---|
| 3,367,324 | 2/1968 | DeBono | 128/2.08 |
| 3,608,546 | 9/1971 | Shinn | 128/2.08 |
| 3,635,214 | 1/1972 | Rand et al. | 128/2.08 |
| 3,722,506 | 3/1973 | McMillan | 128/2.08 |
| 3,735,752 | 5/1973 | Rodder | 128/2.08 |
| 3,774,595 | 7/1973 | Cook | 128/2.08 |
| 3,848,583 | 11/1974 | Parr | 128/2.08 |
| 3,848,584 | 11/1974 | Otsap | 73/239 X |
| 3,848,585 | 11/1974 | Otsap et al. | 128/727 |
| 4,025,070 | 5/1977 | McGill et al. | 272/99 |
| 4,041,935 | 8/1977 | Garbe | 128/727 |
| 4,221,381 | 9/1980 | Ericson | 272/99 |

*Primary Examiner*—Edward M. Coven
*Attorney, Agent, or Firm*—Stanley N. Garber; Andrew J. Beck; William R. O'Meara

[57] ABSTRACT

A spirometer is provided which has a cylinder with a piston slidable in the cylinder. A pair of orifices from the atmosphere to the opposite sides of the piston are provided, the resistance to air flow through them being in a predetermined ratio. A tube is provided for connecting the mouth of a patient to one side of the piston chamber for effecting movement of the piston during inhalation or exhalation. The cylinder is provided with indicia representing units of air volume inhaled or exhaled with the volume of the cylinder being substantially smaller than the volume of air indicated by the spirometer.

12 Claims, 5 Drawing Figures

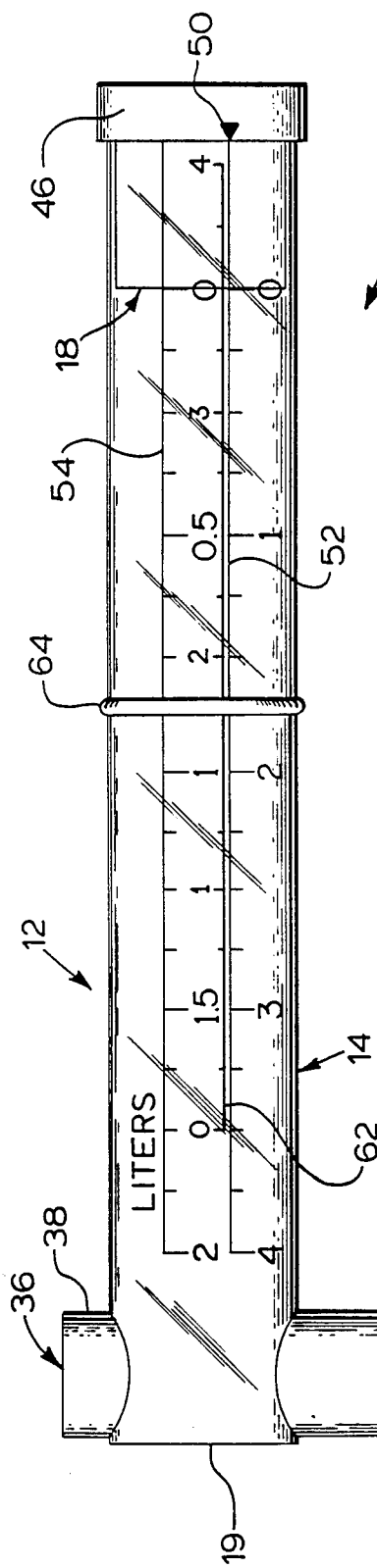
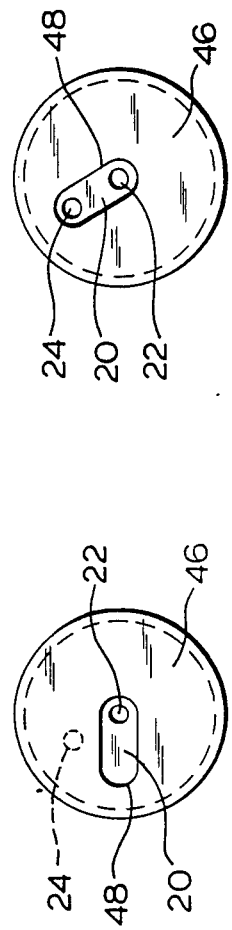
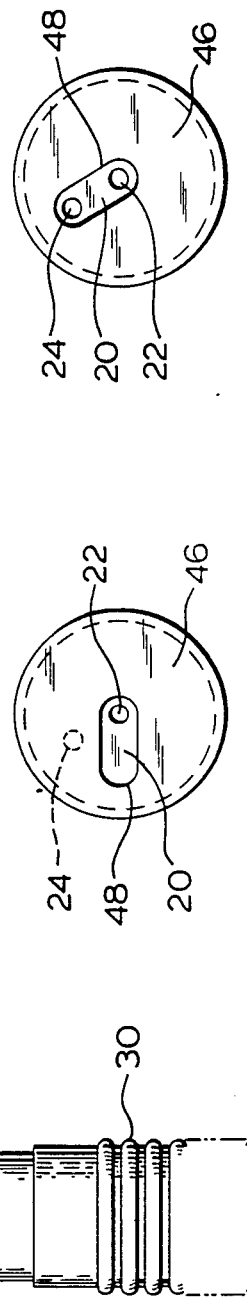

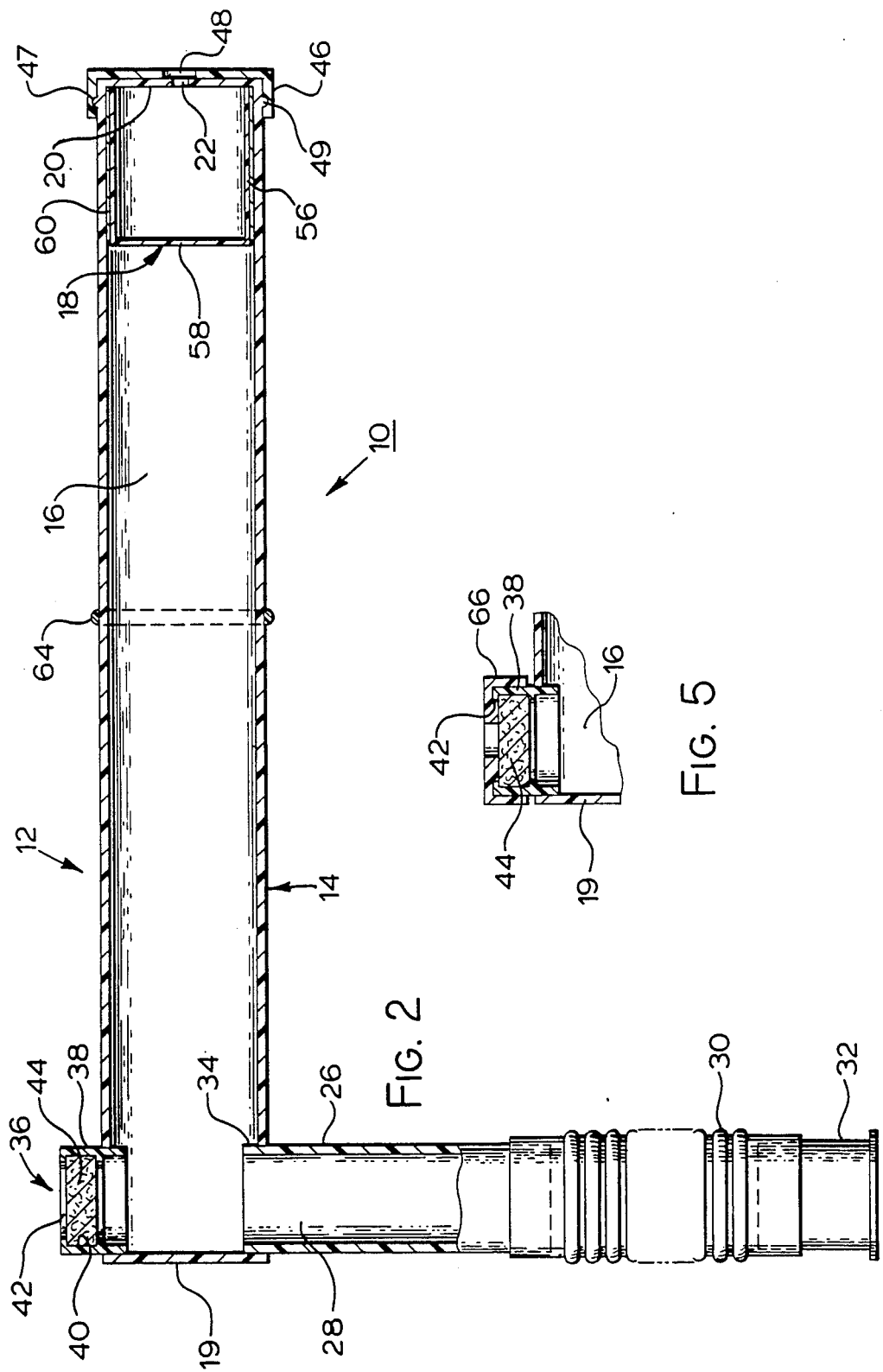

RESPIRATORY DEVICE

DESCRIPTION

1. Technical Field

This invention relates to respiratory devices and, more particularly, to a spirometer for indicating the maximum volume of air inhaled or exhaled by a person during a breathing cycle and which can be used as a breathing exercise device.

2. Background Art

Various respiratory devices are used to monitor or analyze the pulmonary performance of patients and, in some cases, to serve as breathing exercise devices to improve pulmonary function. For example, post-operative patients often require breathing monitoring and exercise to regain their normal breathing functions which may have deteriorated because of the use of general anesthesia or painful surgical wounds. Also, such devices may be used for patients with such diseases as emphysema and bronchitis to measure their pulmonary performance. Some respiratory devices are responsive to air flow rate so as to provide an indication of the breathing effort provided by the patient, but these devices do not provide an indication of the volume of air inhaled or exhaled by the patient. Volume measuring spirometers are often used because it is highly desirable to determine the maximum amount of air inhaled or exhaled during a breathing cycle since the volume of air is directly proportional to the degree of lung expansion or contraction.

One of the problems associated with spirometers has been that they generally include an expansible chamber, for example, a bellows or a piston in a piston chamber, that is made large enough to contain the maximum expected volume of air that the patient may inhale or exhale. This means that the spirometer has to be relatively large and, therefore, cumbersome to handle, especially when it is desirable to keep it at the patient's bedside. For example, in U.S. Pat. No. 3,722,506, the example spirometer had a piston with a diameter of 11 to 12 inches. Other problems associated with such spirometers have been that they are relatively costly to make and, in some cases, it is difficult to determine the measured quantity of air, especially for small volumes of air. Also, many spirometers have been capable of measuring either exhaled or inhaled air but the same spirometer could not conveniently be used to measure both inhaled or exhaled air.

SUMMARY OF THE INVENTION

It is an object of the present invention to provide an improved spirometer which is relatively simple, small and economical in construction, easy to handle and use, provides an indication of the total volume of air inhaled or exhaled, and which overcomes one or more of the above-mentioned problems of the prior art devices.

In accordance with one aspect of the present invention, a spirometer for indicating the total volume of air inhaled or exhaled by a person is provided which includes a chamber, a piston in the chamber, means for connecting the lungs of a person in fluid communication with the chamber on one side of the piston, a main flow resistive orifice connecting the chamber on the one side of the piston to the atmosphere, and a metering orifice connecting the chamber on the opposite side of the piston in fluid communication with the atmosphere.

These, as well as other objects and advantages of the present invention, will be more apparent from the following description and accompanying drawings.

BRIEF DESCRIPTION OF THE DRAWINGS

FIG. 1 is a top plan view of a volumetric spirometer in accordance with a preferred embodiment of the present invention;

FIG. 2 is a cross-sectional view of the spirometer of FIG. 1;

FIG. 3 is a right end view of the volume indicating member of the spirometer of FIG. 1, showing the flow resistance changing device of the indicating member;

FIG. 4 is an end view similar to FIG. 3 but with the resistance changing device rotated to a second position; and FIG. 5 is a cross-sectional view of a portion of a spirometer according to a modified embodiment of the present invention.

BEST MODE FOR CARRYING OUT THE INVENTION

Referring now to the drawings, and more particularly to FIGS. 1 and 2, a volumetric spirometer 10 is shown which can be selectively used to measure the volume of air inhaled and exhaled and will be first described in connection with measuring inhaled volumes of air. Spirometer 10 includes a housing 12 housing a volumetric indicating member shown as a transparent cylinder 14 having an expansible chamber or bore 16. A piston 18 is shown sealingly slidable in chamber 16. The left end of chamber 16 is closed by an end wall 19. The right end of chamber 16 has an end wall 20 which limits rightward movement of piston 18 and closes the chamber except for a pair of piston air control or piston air metering orifices 22 and 24 (FIGS. 3 and 4) which extend through the end wall 20, and which will be further discussed hereafter.

Spirometer 10 is shown including a breathing tube 26 connected at a right angle to the bottom wall of cylinder 14 and which has a chamber or bore 28 connected at the lower end in fluid communication with a flexible tube 30 which, in turn, is connected at its lower end to a patient mouthpiece 32. The upper end portion of tube 26, indicated at 34, extends into the side wall of cylinder 14 and is open to chamber 16. The side of upper end portion 34 serves as a stop for piston 18 should the piston be moved leftwardly that far.

The cylinder 14 is provided with a patient or main air flow resistive passage or orifice, indicated generally at 36. The main orifice 36 is shown including a cylindrical housing 38 secured in the upper side wall of cylinder 14 at the left end of the cylinder. The housing 38 has a chamber 40 and an opening 42 in the upper end of the housing. An air flow restrictive member 44 is disposed in chamber 40 which allows gas or air flow through it but causes a pressure drop across it when air does flow through it. The housing 38, as well as tube 26 are secured in fluid-tight connection with the cylinder 14 by any suitable means, for example, by cement, solvent bonding or welding. The main flow orifice 36 provides a flow resistive air path between the atmosphere and the chamber 16 on the left side of the piston 18 and also with chamber 28.

A piston air metering or control orifice adjusting member, shown as a cup-shaped adjustable end cap 46, is secured for relative rotation to the right end of cylinder 14 and is provided with an opening 48. As seen in FIG. 3, orifice adjusting cap 46 covers metering orifice 24 to prevent air flow through it while metering orifice 22 is uncovered or in registration with opening 48 so that air can flow between chamber 16 on the right-hand side of piston 18 and the atmosphere by way of orifice 22. The orifice 22 is formed to effect a predetermined resistance to air flow through it. In FIG. 4, the end cap 46 is shown rotated clockwise into a second position to uncover orifice 24 so that both metering orifices 22 and 24 provide a restricted air flow path or passage between the atmosphere and chamber 16 on the right-hand side of piston 18, and the effective flow resistance is reduced compared to the flow resistance obtained when the cap is in the position of FIG. 3. The cap 46 is shown having an annular groove 47 receiving an annular integral ring 49 on the periphery of cylinder 14 to allow relative rotation of the cap but prevent it from coming off of the cylinder 14.

As seen in FIG. 1, an indicator member or mark, shown as an arrowhead 50, is predeterminately located on the adjustor cap 46 relative to opening 48, and is used to indicate which of two calibrated inhalation indicia or scales 52 and 54 is to be read, as will be further discussed. The scales 52 and 54 are marked off in units of liters to provide an indication of the total volume of air inhaled by a person or patient using the spirometer 10. When the arrowhead indicator 50 is in alignment with scale 52 as shown, the cap 46 is in the relatively high volume reading position illustrated FIG. 3 and controlled or restricted air flow between the right-hand side of piston 18 and the atmosphere is only through orifice 22. When the cap 46 is rotated to the indicator 50 in alignment with scale 54, both metering orifices 22 and 24 connect chamber 16 on the right side of the piston 18 in restricted fluid communication with the atmosphere. This latter setting may be used, for example, for pediatric service or adult service where the total volume of inhaled air is relatively small. For purposes of illustration, scale 52 is shown calibrated to measure volumes of air from zero to four liters, while scale 54 is marked in units of volume from zero to two liters.

The ratio of the fluid flow resistances between piston control or metering orifice 22 and main flow orifice 36, for a given size chamber 16, determines the calibrated scale markings 52. The ratio of the combined fluid flow resistances of orifices 22 and 24 to that of main orifice 36 determines the calibrated scale markings 54. The volume of chamber 16 can be substantially smaller than the maximum volume inhaled by the patient since some or most of the inhaled air flows into the lungs of the patient from the atmosphere by way of main orifice 36. Preferably, the resistance of main orifice 36 is substantially less than that of metering orifice 22 or metering orifices 22 and 24 combined, so that a substantially greater volume of air breathed by the person using the device flows through main orifice 36. The higher the flow resistance of relatively high resistance metering orifice 22 or orifices 22 and 24 together, compared to the relatively low resistance of main orifice 36, the smaller the piston travel will be for a given volume of air inhaled by the patient. The flow resistance of the piston control or metering orifice may, for example, be about five times or more greater than that of the main orifice and this would provide substantial miniturization of the spirometer. In the illustrated embodiment, orifices 22 and 24 are indicated as being of the same size to produce equal flow resistances and, therefore, the full range of scale 52 is twice that of scale 54.

While various types of differential pressure responsive pistons may be employed, the piston 18 preferably has a relatively low friction, low air leakage, and a small mass. As illustrated in FIG. 2, the piston 18 includes a cylindrical member 56 closed by an end wall 58 at the left end and open at the right end. Disposed about the outer periphery of cylinder 56 is a velour or velvet layer indicated at 60. The cylinder 56 may be made of a suitable plastic, for example, polyethylene or polyvinyl chloride.

In operation, for example, when measuring the total volume of air inhaled by a patient, the cylinder 14 may be held in the hand and shaken to cause the piston 18 to move fully to the right, that is, until it engages end wall 20, if the piston is not already in that position. The adjustor cap indicator 50 is placed in alignment with the desired scale, such as scale 52. After inserting the mouthpiece 32 into the mouth, the cylinder 14 is held in a horizontal position, and the patient inhales, preferably to a maximum degree. This causes air to flow from the chamber 16 on the left side of piston 18 and also from the atmosphere through the relatively low resistance main orifice 36. This flow produces a pressure drop across orifice 36 and a change in pressure on the left side of piston 18 that is proportional to the flow of air, that is, the rate of air flow in the mouthpiece or tube 26 and this effects a pressure differential across piston 18. In this case, the pressure on the left side of piston 18 will be a negative pressure varying in proportion to the air flow. The piston 18 moves leftwardly toward the lower pressure portion of the chamber 16, and air flows through the relatively high resistance orifice 22 in end wall 20 controlling or dampening movement of the piston 18. The velocity of the piston 18 is proportional to the pressure drop and, therefore, to the flow in tube 26, and the total piston displacement, that is, the distance moved from its initial position to its final position after inhalation, is directly proportional to the total volume inhaled by the patient.

The piston displacement is substantially less than the volume of air actually inhaled by the patient so that miniturization of the spirometer is obtained. The volume of air inhaled by the patient is indicated by reading the scale 52 adjacent the leading edge of piston 18 after the inhalation portion of the breathing cycle has taken place. The maximum or total volume of air inhaled by the patient is read directly on the in scale in liters. While various sizes are possible, the total volume of chamber 16 is preferably substantially smaller than the actual maximum volume of air expected to be inhaled or exhaled. A substantial reduction in spirometer size is obtained, for example, when the ratio of the flow resistances between the main flow orifice 36 and the piston air control orifice, such as orifice 22, is such that the volume of air displaced by the piston 18 is less than one-fifth of the actually inhaled volume of air indicated by the scale. The total volume of the cylinder 14 is preferably less than about one-tenth of the maximum volume of actually inhaled or exhaled air. The piston 18 preferably has an outer diameter less than two inches. By such miniturization, the spirometer 10 is substantially easier to handle and use than spirometers which are made large enough to contain the maximum expected inhaled or exhaled air.

Where an adult patient starts out from an especially weakened condition or where a child is to use the spirometer, the flow resistance adjusting cap 46 may be initially rotated until the indicator mark 50 is in alignment with the scale 54, which scale has a maximum reading of two liters and can be more accurately or easily read than scale 54 for smaller volumes of inhaled air. This has the effect of increasing the sensitivity of the spirometer for low volume measurements. Where the breathing capacity of the patient improves so that the volume of air exceeds that of the smaller volume indicated on scale 54, the adjustor end cap 46 is simply rotated so that indicator mark 50 is aligned with the large volume scale 52. The patient can then measure volumes up to four liters instead of two liters in the illustrated embodiment. Thus, the sensitivity of the spirometer 10 is changed when the adjustable flow resistance or adjustable metering orifice at the right end of the chamber 16 is changed, that is, when the ratio of the flow resistance of main orifice 36 to the flow resistance of the variable metering orifice 22, or 22 and 24, is changed.

While only two calibrated scales 52 and 54 for measuring inhalation are shown, a greater number of scales having different volume ranges may be used where desired. The orifice adjustor end cap 46, in such case, can be made to vary the effective resistance to air flowing between the chamber 16 at the right side of piston 18 and the atmosphere, over a greater number of flow resistance values, and a corresponding number of scales could be provided on the cylinder 16. For example, end wall 20 of cylinder 14 could be provided with holes of various sizes or a greater number of like holes that are selectively covered by end cap 46 so as to provide a greater number of effective flow resistance values and scales than shown.

As previously mentioned, spirometer 10 may also be used to measure the total volume of air exhaled by a person. As seen in FIG. 1, a calibrated exhalation scale 62 is provided on cylinder 14, which is reversed from scale 52, that is, it is in volume units which increase left to right from zero to four liters. More than one exhalation scale may, of course, be provided as desired, each having a different volume range.

When employing the spirometer to measure total exhaled air volume, the piston is initially positioned against the stop 34 (FIG. 2) provided by tube 26. Then, after inhaling, the patient exhales into the mouthpiece 32. This flow produces a proportional pressure drop across main orifice 36 and a positive pressure in chamber 16 on the left side of piston 18 that varies in proportion to the air flow through main orifice 36, thereby producing a pressure differential across piston 18 to move the piston.

In this case, restricted air flows rightwardly out of the orifice 22 to the atmosphere. The restriction of air flowing out of orifice 22 controls or dampens the piston movement so that its velocity is proportional to patient air flow. The travel or displacement of piston 18 after exhalation, as indicated by the position of the right end of the piston 18 on scale 62, will provide a direct reading in liters of the actual total volume exhaled. Thus, the spirometer 10 is capable of selectively measuring total volume of air inhaled and exhaled so that either or both volumes can be measured if desired.

Instead of varying the relatively high resistance fluid flow orifice on the right side of piston 18, for example, by increasing the size or number of holes such as accomplished in the embodiment shown in FIGS. 1–4, a fixed or non-variable flow resistance metering orifice may be employed at the right end of chamber 16 on the right side of piston 18, and the relatively low resistance flow path of main orifice 36 at the left side of piston 18 may be varied. For example, as shown in FIG. 5, a mask 66 is shown partially covering the opening 42 to increase the flow resistance of air through the relatively low resistance main orifice 36 on the left side of piston 18. Thus, the mask 66 may be placed over the opening 42 to change the flow resistance ratio of the orifices on the opposite sides of piston 18 when it is desired to employ a different scale.

Making the relatively low resistance main orifice variable to change the sensitivity or scales to be read is desirable in some cases. However, by making the resistance of the high resistance orifice at the right side of the piston variable, the total resistance of the device is affected a lesser amount since the volume of air moved through this orifice is normally substantially less than that through low resistance main orifice 36. The designed total resistance to the flow of air flowing into or out of the mouthpiece 32 as a result of air flowing through the orifices on both sides of the piston 18 generally should not be excessive so as to require too much effort by the patient.

The spirometer 10 is also useful as a breathing exercise device to improve the pulmonary function. By repeatedly measuring the total volume on either one-half portion of the breathing cycle, inhalation or exhalation, the person using the device can determine the improvement in pulmonary function as the exercise continues. For some people, exercise on both inhalation and exhalation portions of the breathing cycle may be beneficial.

A marker or indicator that is manually movable along cylinder 14 but which stays in its position until moved is indicated at 64. The marker 64 is shown as a friction ring or band encircling the cylinder 14. It may be made of a suitable rubber or plastic material. The marker can be used to mark the maximum volume of air inhaled or exhaled during a previous breathing cycle. It can also be positioned to serve as a goal to be reached through continued breathing exercises, and therefore becomes an incentive to the patient to expend a greater effort and thus achieve increases in expansion of his lungs.

The cylinder 14 and tube 26 may be formed of a suitable plastic, such as polypropylene, and which is of a suitable hardness such that cylinder 14 essentially does not change its shape during operation of the device. The flexible tube 30 and mouthpiece 32 may also, of course, be formed of a suitable plastic such as polypropylene or the like. The flow resistance member 44 may be a sponge-like member having cells which allow air to flow through it but which produces a flow resistance to the air flowing through it.

While the restricted flow passages or metering orifices 22 and 24 are illustrated as orifices that effect a resistance to gas or air flow into or out of the chamber 16 on the right-hand side of piston 18, and the flow path or main orifice 36 contains a sponge-like resistance member 44, these fluid flow resistance passages may be formed by various means different from that illustrated as long as they will provide suitable flow resistances and pressure drops across them. Also, the means for varying the flow resistance ratio between the main and metering orifices on opposite sides of piston 18 may take on various forms as will be apparent to those skilled in the art. Various means for varying the effective flow resistance of air in an air passage or passages are well known.

As various changes could be made in the above-described constructions without departing from the scope of the invention, it is intended that all matter contained in the above description and shown in the accompanying drawings be interpreted as illustrative and not in a limiting sense.

I claim:

1. A spirometer comprising a chamber, piston means sealingly slidable in said chamber, first and second air flow resistive orifice means connecting said chamber respectively on one and the opposite sides of said piston means in fluid flow communication with the atmosphere, and passage means for connecting the lungs of a person in fluid communication with said chamber at said one side of said piston means to effect a pressure in said chamber at said one side of said piston means proportional to the flow of air in said passage means generated by the lungs of the person, said piston means being movable in response to the pressure for providing an indication of the total volume of air moved by the lungs, said first orifice means having a first predetermined resistance to air flow therethrough, said second orifice means including means for selectively effecting predetermined second and third resistances to air flow through said second orifice means, each of said second and third resistances being greater than said first predetermined resistance.

2. The spirometer of claim 1 wherein the flow resistance of said second orifice means is at least five times that of said first orifice means.

3. The spirometer of claim 1 wherein said second orifice means includes at least two separate restricted flow passages extending through said chamber to the atmosphere adjacent one end thereof, and means for selectively closing at least one of said passages to effect one of said flow resistances of said second orifice means and opening said one passage to effect the other of said flow resistances of said second orifice means.

4. The spirometer of claim 1 wherein said chamber is elongate and includes end walls closing opposite ends thereof, said first orifice means includes a flow resistance opening means adjacent one of said chamber end walls, and said second orifice means includes a plurality of restricted flow openings, and selectively rotatable means for closing and opening at least one of said openings so that said second orifice means effects said second and third flow resistances.

5. The spirometer of claim 1 wherein said chamber is transparent to enable viewing of said piston means from the exterior of said chamber, and said chamber has indicia including a plurality of different scales extending along the chamber respectively corresponding to said second and third flow resistances whereby the location of said piston means relative to the indicia indicates substantially the volume of air through the device.

6. The spirometer of claim 5 wherein said second orifice means comprises piston air metering passage means extending through said chamber to the atmosphere, and control means selectively movable between first and second positions for selectively varying the effective size of said passage means to change the resistance of said second orifice means from one of said second and third resistances to the other and the travel of said piston means for a given total volume of air moved by the lungs, said control means having indicator means thereon indicating which of said scales corresponds to the selected position and flow resistance of said second orifice means.

7. The spirometer of claim 1 wherein said means for connecting the lungs includes a tube connected in fluid communication to said chamber with its longitudinal axis at an angle to the longitudinal axis of said chamber, said chamber being transparent so that said piston means can be seen by the person using the spirometer.

8. A spirometer for providing an indication of the total volume of air inhaled or exhaled by a person and usable as a respiratory exerciser comprising an elongated chamber adapted to be held in a horizontal position, piston means sealingly slidable in said chamber, main air flow orifice means adjacent one end of said chamber connecting said chamber on one side of said piston means in predetermined resistive fluid flow communication with the atmosphere, a mountpiece adapted to be received in the mouth of a person, means for connecting said mouthpiece in fluid communication with said chamber at said one side of said piston means to effect a fluid pressure drop across said main air flow orifice means proportional to the flow of air in said mouthpiece when air flow is generated by the person during an inhalation or exhalation portion of the breathing cycle, metering orifice means adjacent the opposite end of said chamber connecting said chamber on the opposite side of said piston means with the atmosphere to control the movement of said piston means whereby the velocity of said piston means is proportional to the flow of air through said main air flow orifice and the total displacement of said piston is proportional to the total volume of air exhaled or inhaled by the person, said metering orifice means being selectively variable to effect a plurality of predetermined fixed flow resistances, and said chamber has a plurality of different scales thereon corresponding respectively to said plurality of said flow resistances, each of said flow resistances of said metering orifice means being greater than the flow resistance of said main air flow orifice means so that the total air displaced by said piston means is substantially less than the total volume of air inhaled or exhaled by the person.

9. The spirometer of claim 8 wherein said chamber is transparent so the person inhaling or exhaling can view said piston, and each of said scales is calibrated in units of total volume of air inhaled or exhaled by the person.

10. The spirometer of claim 8 further including a manually movable marker on said chamber.

11. The spirometer of claim 8 wherein said main flow orifice means includes passage means between said chamber and atmosphere which includes a flow resistive material.

12. The spirometer of claim 8 or 11 wherein a removable mask is movable onto said main flow orifice means to increase the resistance thereof.

* * * * *